(12) United States Patent  (10) Patent No.: US 7,654,507 B2
Cortez, Jr. et al.  (45) Date of Patent: Feb. 2, 2010

(54) WATER SPIKE SYSTEM

(75) Inventors: Felino V. Cortez, Jr., Bowie, MD (US); George McGarrity, Denton, MD (US)

(73) Assignee: Vapotherm, Inc., Stevensville, MD (US)

( * ) Notice: Subject to any disclaimer, the term of this patent is extended or adjusted under 35 U.S.C. 154(b) by 0 days.

(21) Appl. No.: 12/048,583

(22) Filed: Mar. 14, 2008

(65) Prior Publication Data
US 2008/0224336 A1 Sep. 18, 2008

Related U.S. Application Data

(60) Provisional application No. 60/918,515, filed on Mar. 16, 2007.

(51) Int. Cl.
*B01F 3/04* (2006.01)
(52) U.S. Cl. .................. 261/4; 96/371; 128/203.21; 261/72.1; 261/121.1; 261/DIG. 65
(58) Field of Classification Search .............. 261/4, 261/72.1, 78.2, 121.1, 122.1, 124, DIG. 65; 128/203, 21, 205.21; 604/122; 96/371
See application file for complete search history.

(56) References Cited

U.S. PATENT DOCUMENTS

| | | | | | |
|---|---|---|---|---|---|
| 3,021,840 | A | * | 2/1962 | Hallamore et al. | 128/200.21 |
| 3,771,721 | A | * | 11/1973 | Van Amerongen | 128/200.18 |
| 3,809,080 | A | * | 5/1974 | Deaton | 128/200.18 |
| 3,825,000 | A | * | 7/1974 | Huggins | 128/200.11 |
| 3,834,385 | A | * | 9/1974 | Pekkarinen | 128/200.11 |
| 3,852,385 | A | * | 12/1974 | Huggins | 261/121.1 |
| 3,857,909 | A | * | 12/1974 | Huggins | 261/64.1 |
| 3,903,216 | A | * | 9/1975 | Allan et al. | 261/78.2 |
| 3,913,843 | A | * | 10/1975 | Cambio, Jr. | 239/338 |
| 4,061,698 | A | * | 12/1977 | Thornwald | 261/78.2 |
| 4,149,556 | A | * | 4/1979 | Schwabe | 137/115.01 |

(Continued)

FOREIGN PATENT DOCUMENTS

DE 22 18 709 10/1973

(Continued)

OTHER PUBLICATIONS

Instruction sheet for Screw Cap Adapter; Hospira 2004 (1 sheet).

(Continued)

*Primary Examiner*—Richard L Chiesa
(74) *Attorney, Agent, or Firm*—RatnerPrestia

(57) ABSTRACT

A kit for coupling a container holding a liquid to a fluid path of a humidifier is disclosed. The kit includes a spike configured to pierce the container and to pass the liquid from the container to a vent through a tube. The vent is configured to vent gas from the liquid while retaining the liquid. The vent has a vent body including an inlet configured for coupling to the tube to receive the liquid from the tube and an outlet configured to pass the liquid to the humidifier. A cap opening is positioned to vent the gas. A filter is positioned over the cap opening to prevent the escape of the liquid therethrough. A cap is coupled to the vent body over the cap opening and has at least one opening therein to allow passage of gas from the opening to atmosphere.

20 Claims, 5 Drawing Sheets

U.S. PATENT DOCUMENTS

| | | | |
|---|---|---|---|
| 4,372,306 A | | 2/1983 | Genese et al. |
| 5,419,316 A | * | 5/1995 | Bernstein ............... 128/203.12 |
| 2002/0092524 A1 | * | 7/2002 | Lockhart et al. ....... 128/203.21 |

FOREIGN PATENT DOCUMENTS

| | | |
|---|---|---|
| EP | 1 219 313 | 7/2002 |
| WO | WO 85/00301 A1 * 1/1985 .......... 261/DIG. 65 |

OTHER PUBLICATIONS

International Search Report for International Application No. PCT/US2008/003432 mailed Aug. 25, 2008.

Written Opinion of the International Searching Authority for International Application No. PCT/US2008/003432 mailed Aug. 25, 2008.

* cited by examiner

WATER SPIKE SYSTEM

CROSS-REFERENCE TO RELATED APPLICATION

The present application claims priority from U.S. Provisional Patent Application Ser. No. 60/918,515, filed on Mar. 16, 2007.

FIELD OF THE INVENTION

The present invention relates to a system for providing liquid to a humidifier to humidify a breathing gas and a method for providing the liquid to the humidifier.

BACKGROUND OF THE INVENTION

Humidifiers for humidifying breathing gases typically use tap water for humidification. The humidifiers may include a closed circulation path for the tap water. For example, the PRECISION FLOW™ high flow, vapor-phase hydration system, available from Vapotherm, Inc. of Stevensville, Md., includes a closed circulation path for water used to humidify breathing gas.

SUMMARY OF THE INVENTION

Briefly, the present invention provides a kit for coupling a container holding a liquid to a fluid path of a humidifier. The kit comprises in combination a spike configured to pierce the container and to pass the liquid from the container and a tube configured for coupling to the spike. The tube is configured to pass the liquid from the spike. A vent is configured to vent gas from the liquid while retaining the liquid. The vent has a vent body comprising an inlet configured for coupling to the tube to receive the liquid from the tube and an outlet configured for coupling to the fluid path of the humidifier to pass the liquid to the humidifier. A cap opening is positioned to vent the gas. A vent passage is in fluid flow communication with the inlet, the outlet, and the cap opening. A filter is positioned over the cap opening to prevent the escape of the liquid through the cap opening. A cap is coupled to the vent body over the cap opening. The cap has at least one opening therein to allow passage of gas from the opening to atmosphere.

The present invention also provides a humidification system comprising a liquid supply and a spike having a spike body including a proximal spike end coupled to the liquid supply, a distal spike end, and a spike lumen extending through the spike body between the proximal spike end and the distal spike end. The spike lumen is in fluid communication with the liquid supply. A tube body includes a proximal tube end coupled to the distal spike end, a distal tube end, and a tube lumen extending through the tube body between the proximal tube end and the distal tube end. The tube lumen is in fluid communication with the spike lumen. A vent body includes a proximal vent end coupled to the distal tube end, a distal vent end, and a vent passage extending through the vent body between the proximal vent end and the distal vent end. The vent passage is in fluid communication with the tube lumen. A humidifier is in fluid communication with the vent passage. The humidifier is adapted to transfer liquid from the liquid supply to a gas being transmitted through the humidifier.

Further, the present invention provides a method of providing liquid from a sterile liquid supply through a coupler assembly to a humidifier. The method comprises the steps of piercing the container with a spike having a passage therethrough to receive the liquid from the container; coupling a tube to the spike to pass the liquid received from the container via the spike; coupling an inlet of a vent body of a vent to the tube to receive the liquid from the tube; coupling an outlet of the vent body to the fluid path of the humidifier to pass the liquid from the vent body to the humidifier; and positioning an opening of the vent body to permit the escape of gas through a filter positioned at the opening and to prevent the escape of the liquid through the opening, while retaining the liquid.

BRIEF DESCRIPTION OF THE DRAWINGS

The foregoing summary, as well as the following detailed description of preferred embodiments of the invention, will be better understood when read in conjunction with the appended drawings, which are incorporated herein and constitute part of this specification. For the purposes of illustrating the invention, there are shown in the drawings an exemplary embodiment of the present invention. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE INVENTION

Figure 1:
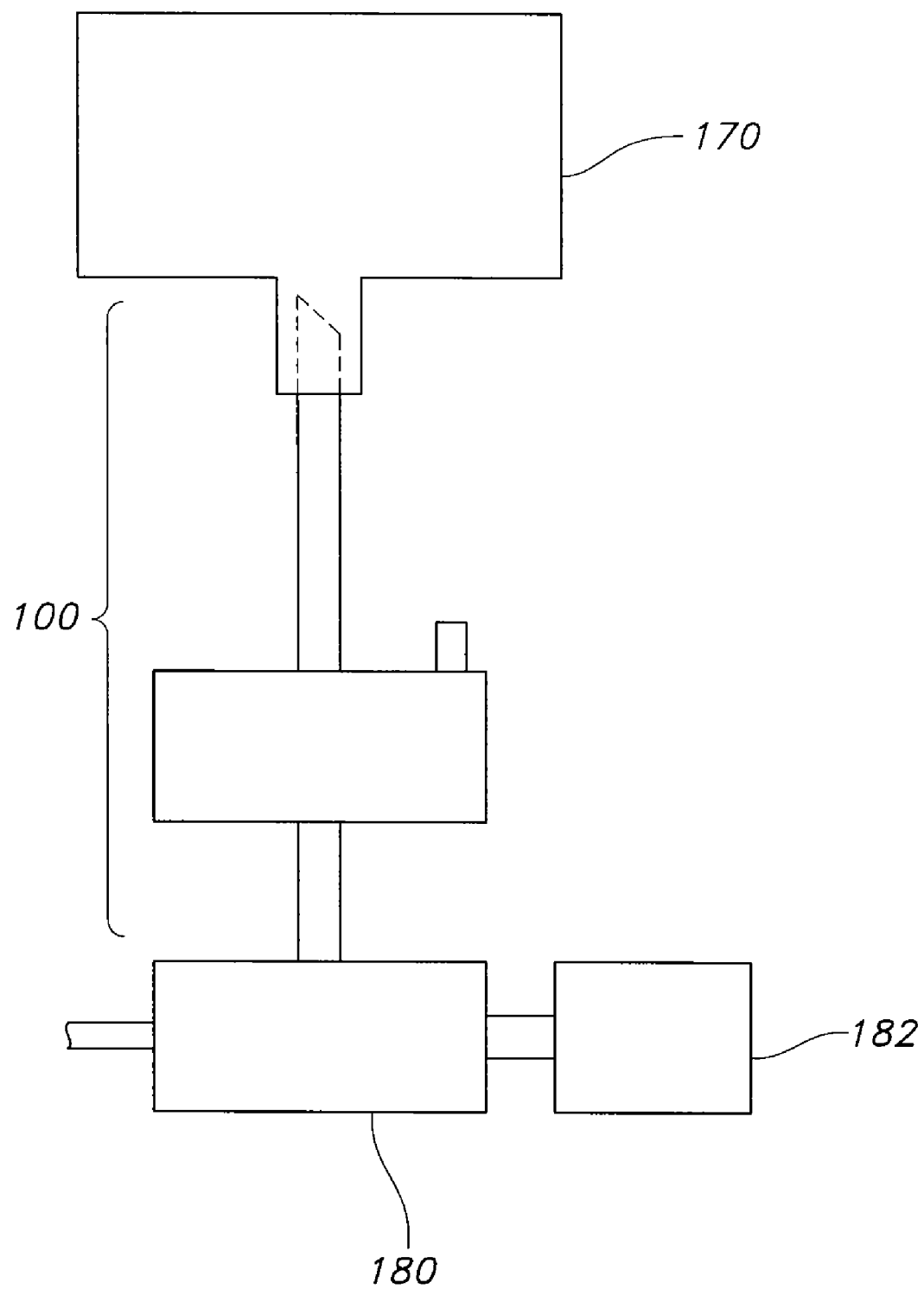
FIG. 1 is a schematic view of an assembly according to an exemplary embodiment of the present invention, in which a liquid supply is connected to a hydration system according to one aspect of this invention.

Certain terminology is used herein for convenience only and is not to be taken as a limitation on the present invention. The terminology includes the words specifically mentioned, derivatives thereof and words of similar import. The following describes an exemplary embodiment of the invention. However, it should be understood based on this disclosure, that the invention is not limited by the exemplary embodiment of the invention.

The present invention provides a kit 100 configured for coupling to a liquid supply 170 and for delivering the liquid to a fluid path of a humidifier 180. Kit 100 includes a spike 110 configured to pierce liquid supply 170 and to facilitate the flow of the liquid from liquid supply 170 and a tube 140 coupled to, or configured to be coupled to, spike 110. Tube 140 is configured for coupling to spike 110. Tube 140 is configured to pass the liquid from spike 110. A vent 150 is configured to vent gas from the liquid and to prevent the escape of the liquid. Vent 150 has a vent body 152 including an inlet 154 configured for coupling to tube 140 to receive the liquid from tube 140. Vent 150 also includes an outlet 156 configured for coupling to the fluid path of humidifier 180 to pass the liquid to humidifier 180. A vent passage 158 is in fluid flow communication with inlet 154, outlet 156, and cap opening 164. A cap opening 160 is positioned in vent 150 to vent gas. A filter 166 is positioned at cap opening 160 to prevent the escape of the liquid through cap opening 160. A cap 162 is coupled to vent body 152 and has at least one opening 164 therein to allow passage of gas from opening 160 to atmosphere.

The present invention also provides a humidification system comprising liquid supply 170 and spike 110 having a spike body 112 including a proximal spike end 114 coupled to liquid supply 170, a distal spike end 116, and a spike lumen 118 extending therethrough between proximal spike end 114 and distal spike end 116. Spike lumen 118 is in fluid communication with liquid supply 170. A tube 140 having a tube body 142 including a proximal tube end 144 is coupled to distal spike end 116. Tube 140 further includes a distal tube end 146 and a tube lumen 148 extending therethrough between proximal tube end 144 and distal tube end 146. Tube lumen 148 is in fluid communication with spike lumen 118. Vent 150 having vent body 152 including proximal vent end 154 is coupled to distal tube end 146. Vent 150 also includes a distal vent end 156 and vent passage 158 extending therethrough between proximal vent end 154 and distal vent end 156. Vent passage 158 is in fluid communication with tube lumen 148. A humidifier 180 is in fluid communication with vent passage 158. Humidifier 180 is adapted to transfer liquid from the liquid supply 170 to a gas being transmitted through humidifier 180.

Further, the present invention provides a method of providing liquid from sterile liquid supply 170 through coupler kit 100 to humidifier 180. The method comprises the steps piercing the container with spike 110 to receive the liquid from the container 170; coupling tube 140 to spike 110 to pass the liquid received from container 170 via spike 110; coupling inlet 154 of vent body 152 of vent 150 to tube 140 to receive the liquid from the tube 140; coupling outlet 156 of vent body 152 to the fluid path of humidifier 180 to pass the liquid from vent body 152 to humidifier 180; and positioning opening 160 of vent body 152 to permit the escape of gas through filter 166 positioned at opening 160 and to prevent the escape of the liquid through opening 160, thereby facilitating the escape of gas from the liquid and preventing the escape of the liquid.

Referring to the Figures in general, a coupler kit 100 that is used to couple a liquid supply 170 to a humidifier 180 is shown. As shown schematically in FIG. 1, coupler kit 100 provides a conduit to allow liquid from a container, such as a liquid supply 170, to be supplied to humidifier 180, such as for humidifying a breathing gas from a gas source 182, which then flows to a patient (not shown) for inhalation. Exemplary humidifiers 180 are the Vapotherm® 2000i and the Vapotherm® Precision Flow™ humidifiers, both available from Vapotherm, Inc. of Stevensville, Md. This humidifier includes a circulating fluid path that includes a vapor transfer cartridge that separates the liquid fluid from the breathing gas and transfers liquid vapor from the liquid fluid to the breathing gas. Coupler kit 100, along with its associated water supply, may be a single patient use item that makes the water side of humidifier 180 a closed system. Liquid supplied with coupler kit 100 may be pre-packaged sterile water that remains sterile as it passes through coupler kit 100. Other suitable liquids will be understood by one of skill in the art from the description herein.

Figure 2:
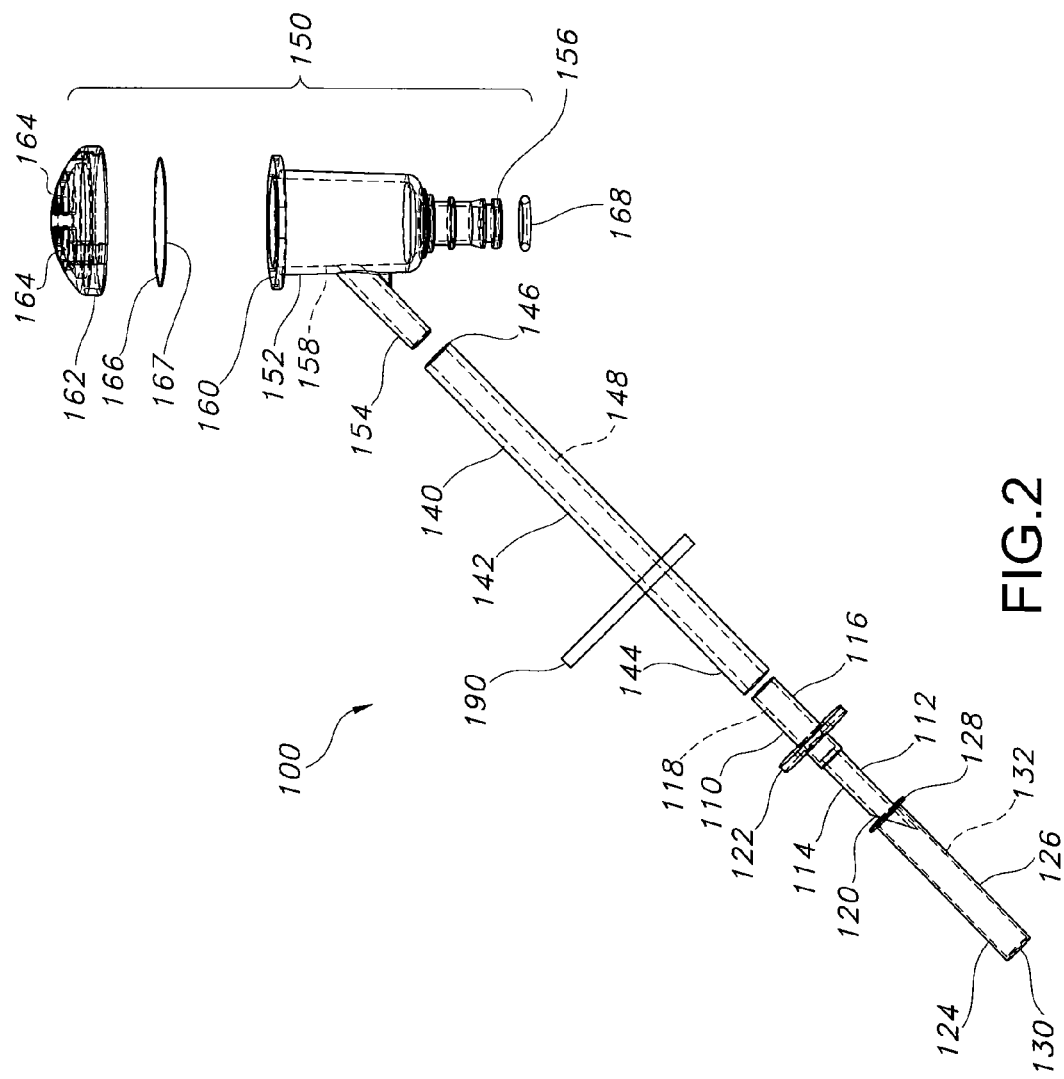
FIG. 2 is an exploded view of a coupler assembly according to an exemplary embodiment of the present invention, which is optionally provided in the form of a kit.
Figure 3:
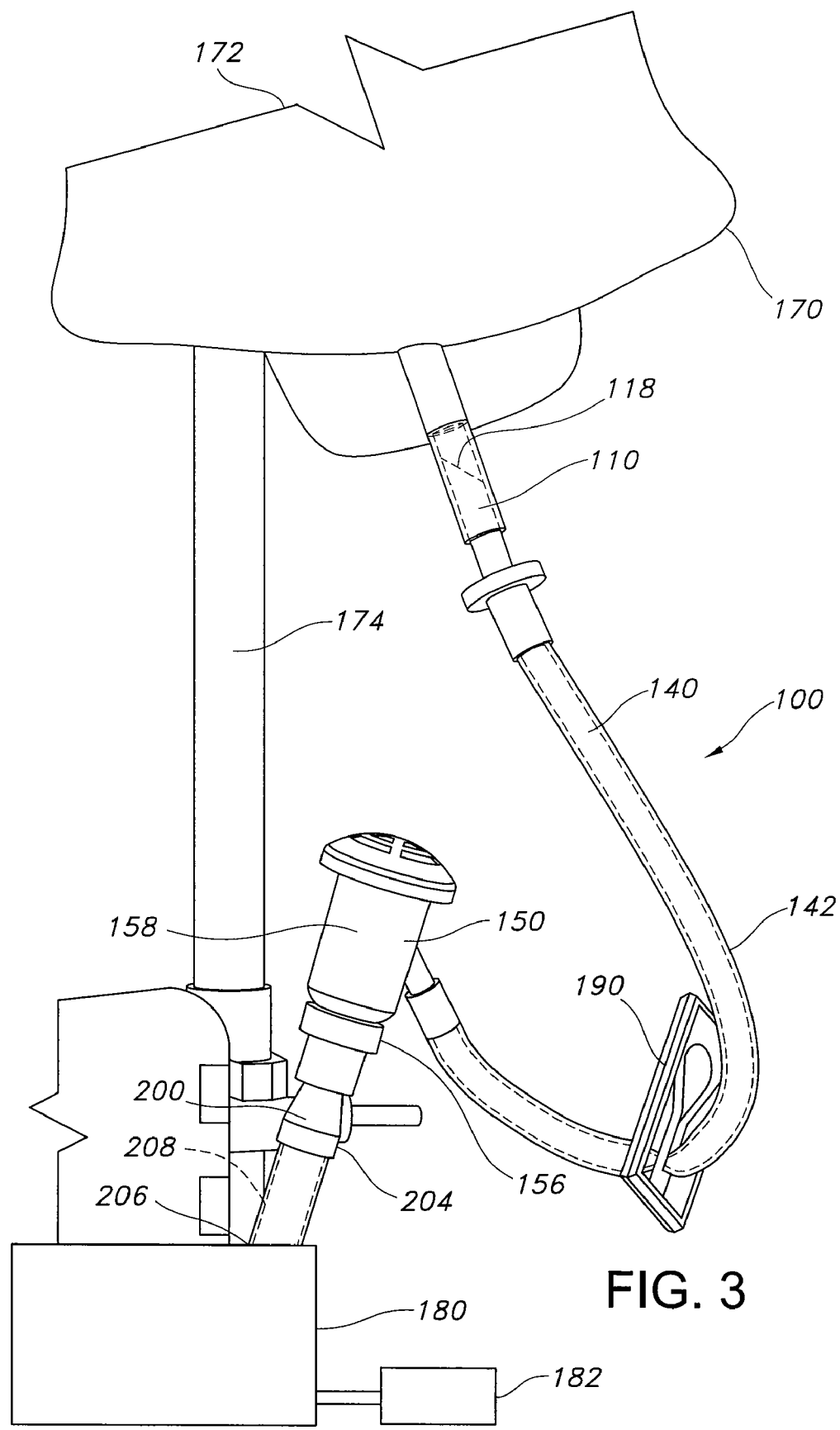
FIG. 3 is a perspective view of the coupler assembly of FIG. 2 connecting a liquid supply to a hydration system.

Referring now to FIGS. 2 and 3, coupler kit 100 includes a spike 110 having a generally tubular spike body 112 with a proximal spike tip 114 and a distal spike outlet 116. A spike lumen 118 extends through body 112 between spike tip 114 and spike outlet 116. Spike tip 114 includes a taper 120 that is inserted into liquid supply 170 to releasably couple spike 110 to liquid supply 170. In an exemplary embodiment, spike body 112 includes a spike collar 122 that extends circumferentially around the exterior of spike body 112 between spike tip 114 and spike outlet 116. Spike 110 may be constructed from ABS polymer, or other suitable biocompatible material. A suitable spike 110 to access intravenous liquid bags will be understood by those skilled in the art of intravenous therapy from the description herein.

A spike cap 124 is releasably disposable over spike tip 114. Spike cap 124 includes a body 126 having an open cap end 128 and a closed cap end 130. A cap lumen 132 extends between open cap end 128 and closed cap end 130. When coupler kit 100 is not coupled to liquid supply 170, spike cap 124 may be inserted over spike tip 114 to reduce risk of contaminating spike tip 114.

Spike tip 114 is inserted into cap lumen 132 through open cap end 128. Spike cap 124 is slid along spike body 112 until open cap end 128 engages spike collar 122. Spike cap 124 is removable from spike 110 when coupler kit 100 is ready for use. Spike cap 124 may be constructed from a polymer or other material, e.g., that is compatible with ETO and gamma ray sterilization.

A tube 140 is configured to couple to spike body 112 and extend from spike outlet 116. Tube 140 includes a tube body 142 having a proximal tube inlet 144, a distal tube outlet 146, and a tube lumen 148 extending between tube inlet 144 and tube outlet 146. In an exemplary embodiment, tube 140 may be flexible vinyl tubing or other suitable biocompatible material.

Tube inlet 144 is inserted over spike outlet 116 so that tube lumen 148 is in fluid communication with spike lumen 118. Tube inlet 144 may be inserted over spike outlet 116 until tube inlet 144 engages spike collar 122.

A vent 150 is configured to couple to tube 180 and extend from tube outlet 146. Vent 150 includes a vent body 152 having a vent passage 158 A proximal vent inlet 154 extends outwardly from vent body 152. Illustrated vent inlet 154 is angled downward, away from vent body 152 at an angle of between about 45 and about 55 degrees from side wall of vent body 152, in order to assist in venting air from tube 140 and to restrict air from entering tube 140, which could preclude liquid flow from tube 140 to vent 150. A distal vent outlet 156 is formed in the bottom of vent body 152 with vent passage 158 providing fluid communication between vent inlet 154 and vent outlet 156.

Vent passage 158 is sufficiently large to hold enough liquid therein such that, when liquid supply 170 is removed from kit 100, such as to replace an empty liquid supply 170 with a full liquid supply 170, liquid remains within vent passage 158 to provide liquid to humidifier 180. In an exemplary embodiment, vent passage 158 has a capacity of about 30 milliliters.

Vent body 152 also includes a vent opening 160 that fluidly communicates with vent passage 158. Vent opening 160 is covered by a vent cap 162 having at least one opening 164 extending therethrough. Vent cap 162 is configured to releasably couple onto vent body 152. Alternatively, vent cap 162 may be secured to vent body by other means, such as an adhesive. Vent body 152 and vent cap 162 may be constructed from transparent polycarbonate material, or other suitable biocompatible material. Vent body may be transparent to allow a user to see bubbles flowing through vent passage 158 and out opening 164 in vent cap 162. In certain humidifiers such as the Vapotherm® 2000i or the Precision Flow™, such bubbles are an indication that a vapor transfer cartridge in humidifier 180 has failed and that humidifier 180 requires service.

Figure 4:
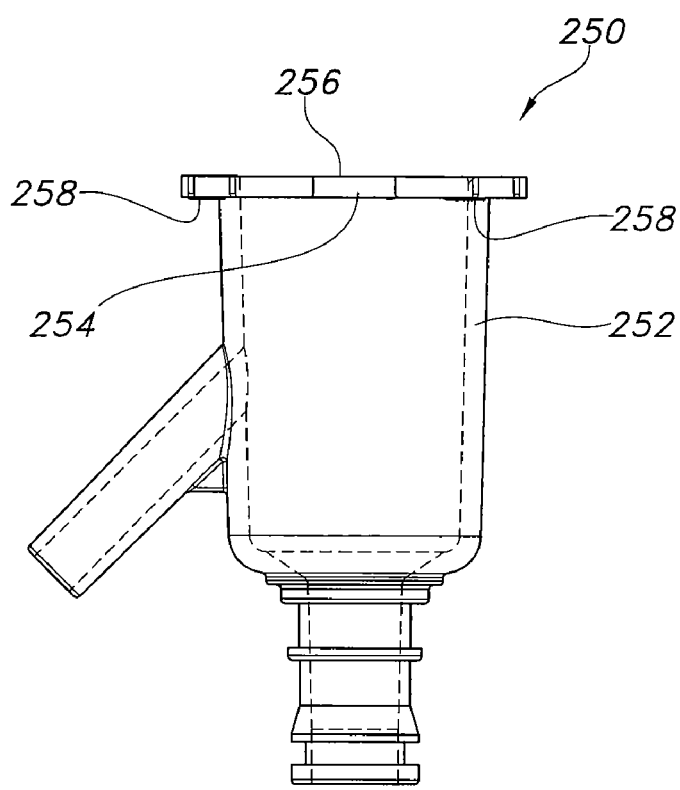
FIG. 4 is a side elevational view of a vent body according to an alternative exemplary embodiment of the present invention.
Figure 5:
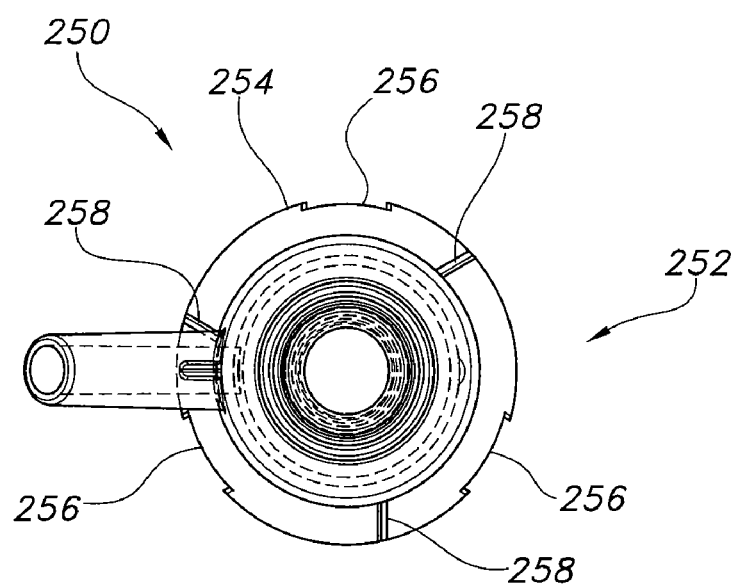
FIG. 5 is a top plan view of the vent body of FIG. 4.
Figure 6:
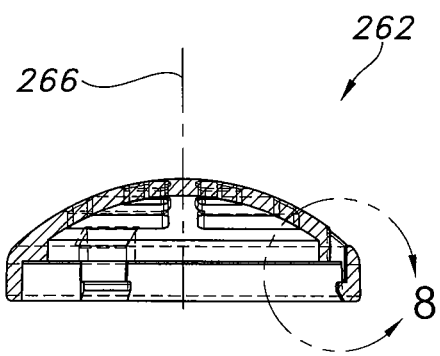
FIG. 6 is a side elevational view of a vent cap associated with the vent body of FIGS. 4 and 5.
Figure 7:
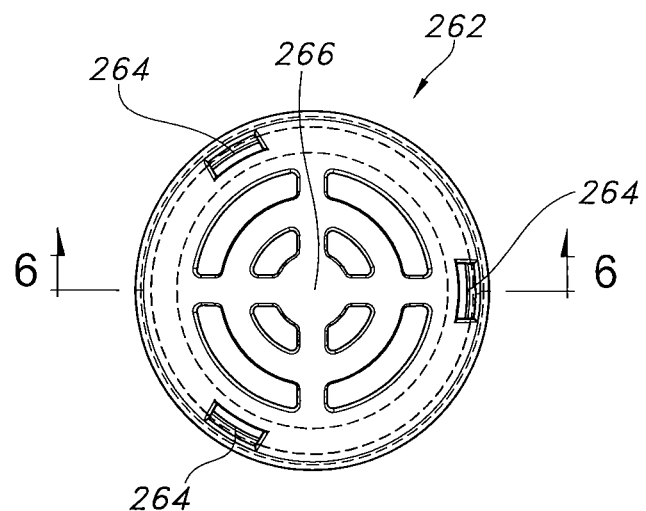
FIG. 7 is a top plan view of the vent cap of FIG. 6.
Figure 8:
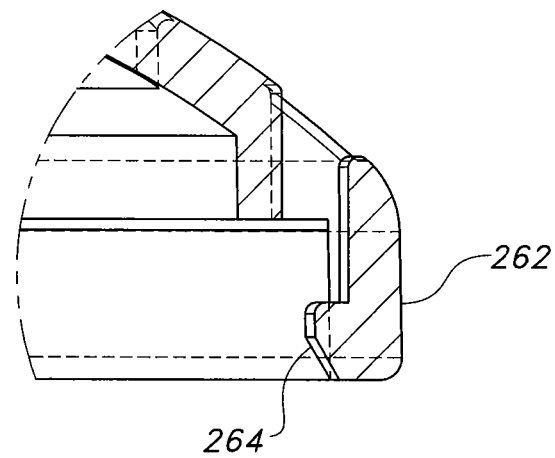
FIG. 8 is an enlarged view of a corner of the vent cap taken along circle 8 of FIG. 6.

An alternative embodiment of a vent 250 is shown in FIGS. 4 and 5, with a cap 262 for use with vent 250 shown in FIGS. 6-8. Cap 262 engages vent 250 in an interlocking relationship to further secure cap 262 to vent 250.

Vent 250 includes a vent body 252 having a lip 254 that extends around a perimeter thereof. Lip 254 includes a plurality of cutouts 256 spaced therearound. In an exemplary embodiment, three cutouts 256 are evenly spaced around the perimeter of lip 254. A plurality of lock bumps 258 extend downward from lip 254. Each lock bump 258 corresponds to a cutout 256 and is spaced a predetermined distance around lip 254 from cutout 256.

Cap 262 is shown in FIGS. 6-8. Cap 262 is similar to cap 162, but includes a plurality of tangs 264 that extend inwardly toward longitudinal axis 266. Each tang 264 corresponds to a cutout 256 in lip 254 of vent 250 and is sized for insertion into a respective cutout 256 when cap 262 is disposed over lip 254. After tangs 264 are inserted into their respective cutouts 256, cap 262 is rotated about longitudinal axis 266 relative to vent 250 until tangs 264 engage lock bumps 258.

Prior to disposing cap 262 over vent 250, an adhesive (not shown) may be applied to top of lip 262 to seal cap 262 onto vent 250.

While the remainder of this disclosure relates to vent 150 and cap 162 in FIGS. 1-3, those skilled in the art will recognize that the disclosure also pertains to vent 250 and cap 262 as well.

A membrane, or filter 166, is disposed within vent 150 between vent cap 162 and vent passage 158. Filter 166 may be constructed from a hydrophobic material, such as expanded polytetrafluoroethylene (ePTFE), so that air is able to pass from vent passage 158 through filter 166, through the at least one opening 164 in vent cap 162, and to atmosphere. Filter 166 includes an adhesive and a vent passage face 167 that allows filter 166 to be adhered to vent body 152. Filter 166 also restricts liquid from vent passage 158 from passing through filter 166 and leaking out of vent 150. In an exemplary embodiment, filter 166 has a diameter of about 25 millimeters, which enables diffusion of a relatively large amount of air from vent passage 158 to atmosphere, e.g., resulting from a failure in humidifier 180.

Tube outlet 146 is slid over vent inlet 154 such that tube lumen 148 is in fluid communication with vent passage 158. Tube 140 may be releasably coupled to vent 150. Vent outlet 156 is releasably couplable to humidifier 180 to provide liquid to humidifier 180. Vent outlet 156 includes an o-ring 168 that engages humidifier 180 to provide a relatively leak-proof seal between vent 150 and humidifier 180.

Referring to FIG. 3, a slide clamp 190 may be disposed over tube body 142 to releasably secure tube 140 and restrict liquid flow from liquid supply 170 to vent 150. A suitable slide clamp 190 will be well known to those of skill in the art from the description herein. Slide clamp 190 is operable between an open position, in which liquid flow is open between liquid supply 170, and humidifier 180, and a closed position, in which liquid flow is restricted between liquid supply 170 and humidifier 180.

Optionally, a supply tube 200 may extend between vent 150 and humidifier 180. Supply tube 200 includes a supply tube inlet 204 coupled to vent outlet 156 and a supply tube outlet 206 coupled to humidifier 180. A supply tube passage 208 extends between supply tube inlet 204 and supply tube outlet 206 to provide fluid communication between vent passage 158 and humidifier 180.

Liquid supply 170 may be sterilized water or other suitable liquid contained in a bag, bottle, or other suitable container, and may be provided in a conventional intravenous bag 172.

In an exemplary embodiment of the use of coupler kit 100, liquid supply 170, in the form of intravenous bag 172, is hung on an intravenous pole 174. Spike 110 is inserted into the intravenous bag 172 so that spike lumen 118 is in fluid communication with the liquid within intravenous bag 172. Vent outlet 156 is coupled to humidifier 180 so that liquid flowing through coupler kit 100 is able to flow into humidifier 180. Initially, clamp 190 is in the closed position so that flow through coupler kit 100 is restricted. After coupler kit 100 is coupled to both liquid supply 170 and humidifier 180, clamp 190 is slid to the open position to allow the liquid to flow primarily via gravity through coupler kit 100 and to humidifier 180. Breathing gas 182 is also directed through humidifier 180 and the sterile liquid is transferred into breathing gas 182 in humidifier 180.

Vent 150 provides venting of liquid within coupler kit 100 to facilitate liquid flow through coupler kit 100, particularly during priming of coupler kit 100, in order to eliminate air within coupler kit 100.

After the liquid drains from liquid supply 170 and liquid supply 170 is empty, coupler kit 100 is de-coupled from liquid supply 170 and empty liquid supply 170 is removed. A replacement liquid supply 170 is provided and coupler kit 100 is coupled to replacement liquid supply 170 in the same manner that coupler kit 100 was coupled to the original liquid supply 170.

Sufficient liquid is retained within vent passage 158 to allow infusion of liquid to humidifier 180 to continue while empty liquid supply 170 is removed and replacement liquid supply 170 is coupled to coupler kit 100.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A kit for coupling a container holding a liquid to a fluid path of a humidifier, the kit comprising in combination:

- a spike configured to pierce the container and to pass the liquid from the container;
- a tube configured for coupling to the spike, the tube configured to pass the liquid from the spike; and
- a vent configured to vent gas from the liquid while retaining the liquid, the vent having:
  - a vent body comprising:
    - an inlet configured for coupling to the tube to receive the liquid from the tube;
    - an outlet configured for coupling to the fluid path of the humidifier to pass the liquid to the humidifier;
    - a cap opening positioned to vent the gas, the cap opening in gas flow communication with the outlet when the kit is in use; and
    - a vent passage in fluid flow communication with the inlet, the outlet, and the cap opening;
  - a filter positioned over the cap opening to prevent the escape of the liquid through the cap opening; and
  - a cap coupled to the vent body over the cap opening, the cap having at least one opening therein to allow passage of gas from the opening to atmosphere.

2. The kit according to claim 1, further comprising a slide valve configured for slidably coupling to the tube for restricting fluid communication through the tube.

3. The kit according to claim 1, further comprising a spike cap removably disposed over the spike.

4. The kit according to claim 1, wherein the outlet is configured to be releasably coupled to a humidifier.

5. The kit according to claim 1, wherein the vent body further comprises a lip extending outwardly from the vent body, the lip comprising a plurality of cutouts, and wherein the cap further comprising a plurality of tangs, each tang being sized to extend through a respective one of the plurality of cutouts.

6. The kit according to claim 1, further comprising a supply tube configured for coupling the vent body outlet to the fluid path of the humidifier.

7. A humidification system comprising:
a liquid supply;
a spike having a spike body including a proximal spike end coupled to the liquid supply, a distal spike end, and a spike lumen extending through the spike body between the proximal spike end and the distal spike end, the spike lumen being in fluid communication with the liquid supply;
a tube body including a proximal tube end coupled to the distal spike end, a distal tube end, and a tube lumen extending through the tube body between the proximal tube end and the distal tube end, the tube lumen being in fluid communication with the spike lumen;
a vent body including a proximal vent end coupled to the distal tube end, a distal vent end, and a vent passage extending through the vent body between the proximal vent end and the distal vent end, the vent passage being in gas communication with the tube lumen and the distal vent end during use of the humidification system; and
a humidifier in fluid communication with the vent passage, wherein the humidifier is adapted to transfer water vapor from the liquid supply to a gas being transmitted through the humidifier.

8. The humidification system according to claim 7, further comprising a supply tube having a proximal supply tube end coupled to the distal vent end, a distal supply tube end coupled to the humidifier, and a supply tube passage extending between the proximal supply tube end and the distal supply tube end, the supply tube passage providing fluid communication between the vent passage and the humidifier.

9. The humidification system according to claim 7, wherein the liquid supply comprises sterilized water.

10. The humidification system according to claim 7, wherein the liquid supply comprises pre-packaged sterile liquid container.

11. The humidification system according to claim 7, wherein the vent body comprises a lip extending outwardly therefrom, the lip comprising a plurality of cutouts and wherein the vent further comprises a cap coupled to the vent body, the cap having at least one opening therein to allow passage of gas from the opening to atmosphere, the cap further comprising a plurality of tangs, each tang being sized to extend through a respective one of the plurality of cutouts.

12. A method for coupling a container holding a liquid to a fluid path of a humidifier, said method comprising the steps of:
a) piercing the container with a spike having a passage therethrough to receive the liquid from the container;
b) coupling a tube to the spike to pass the liquid received from the container via the spike;
c) coupling an inlet of a vent body of a vent to the tube to receive the liquid from the tube;
d) coupling an outlet of the vent body to the fluid path of the humidifier to pass the liquid from the vent body to the humidifier; and
e) positioning an opening of the vent body to permit the escape of gas from the humidifier through a filter positioned at the opening and to prevent the escape of the liquid through the opening, while retaining the liquid.

13. The method according to claim 12, further comprising venting the liquid between the container and the humidifier.

14. The method according to claim 12, wherein the flow of liquid from the container is accomplished primarily via gravity.

15. The method according to claim 12, wherein piercing the container comprises piercing a pre-packaged sterile liquid container.

16. The method according to claim 12, further comprising, after allowing the liquid to flow from the container, removing the spike from the container and piercing a replacement container with the spike.

17. The method according to claim 16, further comprising, after removing the spike, maintaining liquid in the vent body sufficient to continue flowing the liquid from the vent body until the replacement container is pierced with the spike.

18. The method according to claim 12, further comprising, after step e), performing the step of:
f) allowing liquid to flow from the container, through the vent body, and to the humidifier.

19. The method according to claim 18, further comprising, after step f), performing the step of:
g) flowing the breathing gas through the humidifier.

20. The method according to claim 19, further comprising, after step g), performing the step of:
h) transferring water vapor into the breathing gas in the humidifier.

* * * * *